United States Patent
Ohnishi et al.

[11] Patent Number: 6,124,511
[45] Date of Patent: Sep. 26, 2000

[54] METHOD FOR PRODUCING A HYDROGEN-CONTAINING FLUORINATED ALKANE

[75] Inventors: Keiichi Ohnishi; Hidekazu Okamoto, both of Yokohama, Japan

[73] Assignee: Asahi Glass Company Ltd., Tokyo, Japan

[21] Appl. No.: 08/902,969

[22] Filed: Jul. 30, 1997

[30] Foreign Application Priority Data

Aug. 6, 1996 [JP] Japan .................................. 8-207384
Aug. 28, 1996 [JP] Japan .................................. 8-227082

[51] Int. Cl.⁷ .................................................. C07C 17/08
[52] U.S. Cl. ............................................ 570/167; 570/168
[58] Field of Search ..................................... 570/167, 168

[56] References Cited

U.S. PATENT DOCUMENTS 2,768,983 10/1956 Couper et al. .
2,875,254 2/1959 Gradishar .

FOREIGN PATENT DOCUMENTS

| 853297 | 11/1960 | United Kingdom . |
| 975498 | 11/1964 | United Kingdom . |
| WO 91/18853 | 12/1991 | WIPO . |
| WO 94/06554 | 3/1994 | WIPO . |

*Primary Examiner*—Alan Siegel
*Attorney, Agent, or Firm*—Oblon, Spivak, McClelland, Maier & Neustadt, P.C.

[57] ABSTRACT

A method for producing a hydrogen-containing fluorinated alkane, which comprises fluorinating at least one halogenated hydrocarbon selected from a chlorinated ethylene and a hydrogen-containing chlorinated alkane by hydrogen fluoride in the presence of a fluorination catalyst, in a reaction system where a corrosion-resistant metal material containing at least 10 wt % of aluminum, is present.

18 Claims, No Drawings ns fluorinated alkanes which present no or little# METHOD FOR PRODUCING A HYDROGEN-CONTAINING FLUORINATED ALKANE The present invention relates to a method for producing a hydrogen-containing fluorinated alkane in a reaction system where a corrosion-resistant metal material is present.

Heretofore, a chlorofluorocarbon such as trichlorofluoromethane (CFC-11), dichlorodifluoromethane (CFC-12) or trichlorotrifluoroethane (CFC-113) has been used, for example, as a blowing agent, as a cleaning agent or as a refrigerant for e.g. refrigeration or air conditioning. However, such no hydrogen-containing chlorinated alkanes are regulated as compounds which destroy the ozone layer. Accordingly, efforts have been made to develop hydrogen-containing fluorinated alkanes which present no or little influence to the ozone layer.

For example, 2,2-dichloro-1,1,1-trifluoroethane (HCFC-123) is a compound useful as a refrigerant for a centrifugal chiller or as an intermediate for 2-chloro-1,1,1,2-tetrafluoroethane (HCFC-124) or pentafluoroethane (HCFC-125). Further, 1,1,1,3,3-pentafluoropropane (HFC-245fa) is a hydrogen-containing fluorinated alkane which is useful as e.g. a blowing agent and which does not destroy the ozone layer.

As a corrosion-resistant reactor to be used for the production of hydrogen-containing fluorinated alkanes, (1) one containing at least one metal selected from gold, platinum, palladium, molybdenum, rhenium and tungsten (Japanese PCT Patent Publication JP-8-501551) or (2) a reactor having a resin lining (JP-A-6-244195) has been known.

As a method for producing CFC-11, 12, 113 or the like, a reaction to fluorinate a chlorinated alkane or a chlorinated alkene by hydrogen fluoride in the presence of a fluorination catalyst, is known. If this reaction is applied to a reaction to obtain a hydrogen-containing fluorinated alkane, corrosion of the apparatus will be so high that with conventional materials for the apparatus, such as commonly used stainless steel materials, wear of the apparatus by corrosion is vigorous, and such materials are industrially useless due to deterioration of the installation.

Further, nickel alloys such as Hastelloy (tradename), Inconel (tradename) and Monel (tradename) which are commonly used as corrosion-resistant materials and recommended as materials for reactors in WO96/01797, also undergo substantial corrosion, and their corrosion levels are not yet sufficient for industrial use, although corrosion may be reduced as compared with stainless steel materials. The above mentioned stainless steel materials contain no aluminum, and the aluminum content of the above mentioned nickel materials is known to be at a level of 4 wt % at the maximum.

Further, a metal salt of the material of the apparatus formed by corrosion is likely to act as a catalyst poison and hinder catalytic activities, or when the material of the apparatus undergoes corrosion, the catalyst is likely to be reduced and lose the catalytic activities. Thus, the corrosion is likely to adversely affect the catalytic activities.

On the other hand, the corrosion-resistant materials mentioned in the above item (1) are all very expensive and not suitable as materials for large size reaction apparatus of an industrial scale. The material for the reactor in the item (2) is one having a resin lining formed on the inner wall of the reactor, but the resin lining has a drawback that as compared with a metal, its thermal conductivity is low, and the temperature control for the reaction tends to be difficult.

It is an object of the present invention to overcome the drawbacks of the prior art and to provide an improved method for producing a hydrogen-containing fluorinated alkane by means of a reactor excellent in corrosion resistance, made of a material which is relatively inexpensive and readily industrially available.

The present invention provides a method for producing a hydrogen-containing fluorinated alkane, which comprises fluorinating at least one halogenated hydrocarbon selected from a chlorinated ethylene and a hydrogen-containing chlorinated alkane by hydrogen fluoride in the presence of a fluorination catalyst, in a reaction system where a corrosion-resistant metal material containing at least 10 wt % of aluminum, is present.

Now, the present invention will be described in detail with reference to the preferred embodiments.

In the present invention, as a corrosion-resistant metal material present in the reaction system, typically as the material for the inner surface of a reactor, a corrosion-resistant metal material containing at least 10 wt % of aluminum is used which is excellent in corrosion resistance. The preferred proportion of aluminum in the corrosion-resistant metal material is at least 20 wt %, particularly at least 30 wt %.

The upper limit of the proportion of aluminum is a proportion such that the corrosion-resistant metal material consists substantially solely of aluminum. The corrosion-resistant metal material consisting substantially solely of aluminum means that the material may contain a very small amount of metal impurities other than aluminum which may be included during the production.

By using a reactor having an inner surface made of this corrosion-resistant metal material, it is possible to reduce deterioration of the apparatus by corrosion and to continue the reaction with good results over a long period of time without losing the catalytic activities.

This corrosion-resistant metal material may be used by itself as a material for the reactor, or it may be used for a composite material comprising at least one of such corrosion-resistant metal materials as a surface material (hereinafter referred to as a cladding material) and at least one of other materials as a substrate (hereinafter referred to as a core material) constituting a base of the corrosion-resistant metal material.

The core material is not particularly limited so long as it is one which satisfies various properties required for the reactor other than corrosion resistance, such as the strength, weldability and thermal conductivity. Usually, carbon steel, stainless steel, a nickel alloy or aluminum may, for example, be used. To improve e.g. the adhesion of the core material and the corrosion-resistant metal material, the core material may be made to have two or more layers. As a method for preparing the composite material, a method may, for example, be mentioned wherein the corrosion-resistant metal material is complexed to the core material by such a method as plating, flame coating or explosion cladding.

To protect the core material from a corrosive environment, the corrosion-resistant material used as the claddig material is preferably in the form of a dense layer free from cracks, and its thickness varies depending upon the preparation method and the corrosion-resistant metal material selected and is not particularly limited. However, taking the durability and mechanical strength of the material into consideration, it should better have a certain thickness, i.e. preferably from 10 $\mu$m to 30 mm, more preferably from 30 $\mu$m to 10 mm, most preferably from 100 $\mu$m to 10 mm.

In general, the surface of the corrosion-resistant metal material is covered by a metal oxide to form a passive state. In the fluorination reaction of the present invention, at least a part of the surface of the corrosion-resistant metal material is preferably covered by a protective layer containing a metal fluoride. This is particularly preferred in the case of a corrosion-resistant metal material containing a metal component having a relatively low standard oxidation-reduction potential, such as aluminum. A more stable passive state will be formed by the surface covered with a protective film containing a metal fluoride, whereby excellent corrosion resistance will be obtained even in a superacidic condition like the fluorination reaction system of the present invention.

The protective layer containing a metal fluoride is preferably formed prior to the reaction, but such a protective layer may be formed during the reaction. To form the protective layer containing a metal fluoride at least prior to the reaction, a reactor with its inner surface covered with a corrosion-resistant metal material may be treated with a suitable fluorinating agent.

Such a fluorinating agent is not particularly limited, and it may, for example, be fluorine gas, hydrogen fluoride or antimony pentafluoride. The treating temperature may vary depending upon the corrosion-resistant metal material. However, in the case of fluorine gas, the treating temperature may preferably be from 0° C. to 300° C., more preferably from room temperature to 200° C., and the fluorine gas is usually adjusted by an innert gas such as nitrogen to a concentration of fluorine gas of from 20 to 100 vol %.

In the case of hydrogen fluoride, the treating temperature is preferably from 0° C. to 300° C., more preferably from room temperature to 300° C., and anhydrous hydrogen fluoride is used in the form of liquid or gas. In the case of antimony pentafluoride, the treating temperature is preferably from 0° C. to 200° C., more preferably from room temperature to 120° C. These fluorinating agents may be used alone, or two or more of them may be used at the same time or sequentially.

In the corrosion-resistant metal material containing aluminum as a corrosion-resistant component, the corrosion-resistant component in the fluorination reaction environment of the present invention is essentially an aluminum-containing fluoride present on the very surface of the corrosion-resistant metal material. Accordingly, the amount of the aluminum component required to form such a fluoride protective layer at the surface of the corrosion-resistant metal material may be small, and adequate effects can be obtained even with a content of about 10 wt % as the metal component in the corrosion-resistant metal material.

As components other than aluminum in the corrosion-resistant metal material, metal components commonly used for metal materials, may be used. Particularly preferred is at least one component selected from iron, copper, manganese, cobalt and chromium. It is preferred that such components other than aluminum are in the form of an alloy with aluminum. A preferred alloy may, for example, be an Al—Cu—Mn alloy, an Al—Cu—Mn—Mg alloy, an Al—Mg—Cr alloy, an Al—Mg—Mn alloy, a Fe—Cr—Al alloy, a Fe—Cr—Al—Co alloy or a Cu—Al alloy.

The corrosion-resistant metal material containing at least 10 wt % of aluminum may be pure aluminum for industrial use, or may be a material containing at least 10 wt % of aluminum and at least one subsidiary component selected from iron, copper, manganese, magnesium, cobalt and chromium. Especially the latter is improved over pure aluminum for industrial use in a characteristic such as strength and can be used not only as a cladding material but also as a core material for a reactor.

The reaction to obtain the desired hydrogen-containing fluorinated alkane by fluorinating at least one halogenated hydrocarbon selected from a chlorinated ethylene and a hydrogen-containing chlorinated alkane by hydrogen fluoride, can be carried out in a gas phase or in a liquid phase, in the presence of a fluorination catalyst. It is preferred to carry out the reaction in a liquid phase in the presence of a fluorination catalyst in order to obtain the desired hydrogen-containing fluorinated alkane in good yield while suppressing a side reaction to form an olefin.

The chlorinated ethylene to be used as a starting material is a halogenated hydrocarbon of the formula (1) $C_2H_aF_bCl_c$ wherein a, b and c are integers satisfying $a+b+c=4$, $a \geq 0$, $b \geq 0$ and $c \geq 1$.

The hydrogen-containing chlorinated alkane is meant for a compound having some of hydrogen atoms of a saturated hydrocarbon substituted by chlorine atoms, and it is preferably a compound having from 1 to 6 carbon atoms. Some of hydrogen atoms of the saturated hydrocarbon may be substituted by fluorine atoms as well as chlorine atoms.

Preferred hydrogen-containing chlorinated alkanes are a hydrogen-containing chlorinated methane of the formula (2) $CH_dF_eCl_f$ wherein d, e and f are integers satisfying $d+e+f=4$, $d \geq 1$, $e \geq 0$ and $f \geq 1$, a hydrogen-containing chlorinated ethane of the formula (3) $C_2H_gF_hCl_i$ wherein g, h and i are integers satisfying $g+h+i=6$, $g \geq 1$, $h \geq 0$ and $i \geq 1$, and a hydrogen-containing chlorinated propane of the formula (4) $C_3H_mF_nCl_p$ wherein m, n and p are integers satisfying $m+n+p=8$, $m \geq 1$, $n \geq 0$ and $p \geq 1$.

Usually, the positions of hydrogen atoms and fluorine atoms in the starting material will not change in the product. The positions of chlorine atoms in the starting material will not change in the product or such chlorine atoms will be substituted by fluorine atoms without changing their positions. However, in some cases, the positions of respective atoms may change as between before and after the reaction due to a disproportionation reaction which may take place.

The desired hydrogen-containing fluorinated alkane is a compound having some or all of chlorine atoms in the starting material halogenated hydrocarbon substituted by fluorine atoms.

In a case where the starting material halogenated hydrocarbon is a compound of the above formula (1), the desired preferred hydrogen-containing fluorinated alkane is a hydrogen-containing fluorinated ethane of the formula (5) $C_2H_{a+1}F_{b+1+w}Cl_{c-w}$ wherein a, b, c and w are integers satisfying $a+b+c=4$, $a \geq 0$, $b \geq 0$, $c \geq 1$ and $0 \leq w \leq c$.

In the formula (1), a, b and c are preferably integers satisfying $a+b+c=4$, $0 \leq a \leq 3$, $0 \leq b \leq 2$ and $1 \leq c \leq 4$, and in the formula (5), a, b, c and w are preferably integers satisfying $a+b+c=4$, $0 \leq a \leq 3$, $0 \leq b \leq 2$, $1 \leq c \leq 4$ and $1 \leq w \leq 4$.

In a case where the starting material halogenated hydrocarbon is a hydrogen-containing halogenated methane of the above formula (2), the desired preferred hydrogen-containing fluorinated alkane is a hydrogen-containing fluorinated methane of the formula (6) $CH_dF_{e+x}Cl_{f-x}$ wherein d, e, f and x are integers satisfying $d+e+f=4$, $d \geq 1$, $e \geq 0$, $f \geq 1$ and $1 \leq x \leq f$.

In the formula (2), d, e and f are preferably integers satisfying $d+e+f=4$, $1 \leq d \leq 3$, $0 \leq e \leq 1$ and $1 \leq f \leq 3$, and in the formula (6), d, e, f and x are preferably integers satisfying $d+e+f=4$, $1 \leq d \leq 3$, $0 \leq e \leq 1$, $1 \leq f \leq 3$ and $1 \leq x \leq 3$.

In a case where the starting material halogenated hydrocarbon is a compound of the above formula (3), the desired preferred hydrogen-containing fluorinated alkane is a hydrogen-containing fluorinated ethane of the formula (7) $C_2H_gF_{h+y}Cl_{i-y}$ wherein g, h, i and y are integers satisfying $g+h+i=6$, $g \geq 1$, $h \geq 0$, $i \geq 1$ and $1 \leq y \leq i$.

In the formula (3), g, h and i are preferably integers satisfying $g+h+i=6$, $1 \leq g \leq 4$, $0 \leq h \leq 3$ and $1 \leq i \leq 4$, and in the formula (7), g, h, i and y are preferably integers satisfying g+h+i=6, $1 \leq g \leq 4$, $0 \leq h \leq 3$, $1 \leq i \leq 4$ and $1 \leq y \leq 4$.

Preferred combinations of the above "starting material/desired product" include, for example, "tetrachloroethylene/1,1-dichloro-2,2,2-trifluoroethane", "trichloroethylene/1-chloro-2,2,2-trifluoroethane", "vinylidene chloride/1,1,1-trifluoroethane", "vinyl chloride/1,1-difluoroethane" and "1,1,1-trichloroethane/1,1,1-trifluoroethane".

In a case where the starting material halogenated hydrocarbon is a compound of the above formula (4), the desired preferred hydrogen-containing fluorinated alkane is a hydrogen-containing fluorinated propane of the formula (8) $C_3H_mF_{n+z}Cl_{p-z}$ wherein m, n, p and z are integers satisfying m+n+p=8, $m \geq 1$, $n \geq 0$ $p \geq 1$ and $1 \leq z \leq p$.

In the formula (4), m, n and p are preferably integers satisfying m+n+p=8, $1 \leq m \leq 4$, $0 \leq n \leq 5$ and $1 \leq p \leq 6$, and in the formula (8), m, n, p and z are preferably integers satisfying m+n+p=8, $1 \leq m \leq 4$, $0 \leq n \leq 5$, $1 \leq p \leq 6$ and $1 \leq z \leq 6$.

Preferred combinations of the above "starting material/desired product" include, for example, "at least one selected from a partial fluoride of 1,1,1,3,3-pentachloropropane and 1,1,1,3,3-pentachloropropane/1,1,1,3,3-pentafluoropropane".

The partial fluoride of 1,1,1,3,3-pentachloropropane means a compound having some of chlorine atoms in 1,1,1,3,3-pentachloropropane substituted by fluorine atoms. For example, it may be 1,1,3,3-tetrachloro-1-fluoropropane, 1,3,3-trichloro-1,1-difluoropropane, 3,3-dichloro-1,1,1-trifluoropropane or 3-chloro-1,1,1,3-tetrafluoropropane.

The partial fluoride of 1,1,1,3,3-pentachloropropane is a fluorinated intermediate formed as a byproduct together with the desired 1,1,1,3,3-pentafluoropropane, and after separation from the desired product and purification, it may be used independently or together with 1,1,1,3,3-pentachloropropane as the starting material.

1,1,1,3,3-pentachloropropane can readily be prepared by a radical addition reaction of carbon tetrachloride with vinyl chloride as a commonly used monomer.

As the fluorination catalyst, for the gas phase reaction, a fluorination catalyst such as chromia, alumina or magnesia is usually employed, and for the liquid phase reaction, a fluorination catalyst containing a metal halide of at least one element selected from antimony, niobium and tantalum is usually employed.

As the halide, a chloride, a fluoride or a chlorofluoride is preferred. Specifically, $SbF_5$, $SbCl_5$, $SbCl_2F_3$, $NbCl_5$, $NbClF_4$, $NbF_5$, $TaF_5$, $TaCl_5$ or $TaClF_4$ may, for example, be preferred. These halides may be used in combination as a mixture of two or more which are different in the type of elements or in the type of halogens. Further, a catalyst containing a halide of an element such as Ti or Sn in addition to the halide of the above mentioned element, may also be used. The amount of the above fluorination catalyst is not particularly limited.

The liquid phase fluorination reaction is carried out under atmospheric pressure or elevated pressure. The reaction temperature is preferably from 0° C. to 175° C., more preferably from 20 to 120° C. The reaction is carried out usually by using the starting material for reaction or the reaction product as a solvent for reaction. However, other solvent for reaction may be employed. Such other solvent for reaction is not particularly limited so long as it is capable of dissolving the starting material and the solvent itself is less susceptible to fluorination than the starting material. Such a solvent may, for example, be a perfluoropolyether, a perfluorocarbon such as perfluorooctane, or a hydrofluorocarbon other than the reaction product.

The molar ratio of hydrogen fluoride supplied to at least one halogenated hydrocarbon selected from a chlorinated ethylene, a hydrogen-containing chlorinated ethane and a hydrogen-containing chlorinated methane as the starting material, is not particularly limited so long as it is at least stoichiometrical amount. Taking into consideration the reactor efficiency or the loss during the recovery of hydrogen fluoride, it is preferably within a range of from 1 to 10 mols, more preferably from 1 to 5 mols, to the stoichiometrical amount.

Hydrogen fluoride may be charged preliminarily prior to the reaction or may be blown into the liquid phase at the time of reaction. The pressure for reaction is usually from 0 to 20 kg/cm²G. However, in a case where a solvent for reaction other than the starting material for reaction or the reaction product, is employed, the reaction pressure may vary depending upon the type of the solvent.

Now, the present invention will be described in further detail with reference to Examples. However, it should be understood that the present invention is by no means restricted to such specific Examples.

EXAMPLE 1

The interior of a 2l autocrave having an inner surface consisting substantially solely of aluminum, was evacuated under reduced pressure at 120° C., and then a fluorine gas diluted to 20% with nitrogen, was introduced into the autocrave at 50° C. The supply of the diluted fluorine gas was continued for 4 hours, while purging under atmospheric pressure. Then, a fluorine gas diluted to 50% with nitrogen was sealed in the autocrave, and the temperature was raised to 200° C. and then maintained for 2 hours. After cooling to room temperature, the remaining fluorine gas was purged with nitrogen gas, and 800 g of $SbF_5$ and 400 g of hydrogen fluoride were charged.

The autocrave was heated to 100° C., and then a reaction was initiated by supplying tetrachloroethylene at an average supply rate of 80 g/hr (0.48 mol/hr) and hydrogen fluoride at an average supply rate of 60 g/hr (3 mol/hr) with stirring. The pressure for reaction was controlled to be from 11 to 12 kg/cm²G, and the product was continuously distilled out together with hydrogen chloride produced as a byproduct and unreacted hydrogen fluoride from a condenser maintained at 90° C.

Organic components in the distilled gas after 24 hours are shown in Table 1 (unit: mol %). The reaction was terminated after 72 hours, and the inner surface consisting substantially solely of aluminum was inspected, whereby no corrosion was observed.

EXAMPLE 2

The interior of a 2l autocrave having an inner surface consisting substantially solely of aluminum was evacuated under reduced pressure at 120° C. Then, 100 g of hydrogen fluoride was charged into the autocrave at room temperature. The temperature was raised to 120° C. and then maintained for one hour. Then, hydrogen fluoride in the autocrave was purged, and nitrogen gas was introduced. After cooling the autocrave to room temperature, 800 g of $SbF_5$ and 400 g of hydrogen fluoride were charged.

The autocrave was heated to 100° C., and then the reaction was initiated by supplying methylene chloride at an average supply rate of 100 g/hr and hydrogen fluoride at an average supply rate of 55 g/hr with stirring. The pressure for reaction was controlled to be 10 kg/cm²G, and the product was continuously distilled out together with hydrogen chloride produced as a byproduct and unreacted hydrogen fluoride from a condenser maintained at 80° C.

Organic components in the distilled gas after 24 hours are shown in Table 1. The reaction was terminated after 72 hours, and the inner surface consisting substantially solely of aluminum was inspected, whereby no corrosion was observed.

In the following Examples 3 to 17, several types of test piece metals for corrosion tests were evaluated to determine whether or not the metal species of the test pieces were useful as a metal material for the inner surface of a reactor to be used for the reaction system of the present invention. As a result, it was found that the corrosion rate of a test piece metal containing at least 10 wt % of aluminum was very low, and such a metal is suitable as a metal material for the inner surface of a reactor to be used for the reaction system of the present invention, like the results of the above Examples 1 and 2.

EXAMPLE 3

A test piece for corrosion test of about 40 mm×10 mm×3 mm was attached to the inside of a 2l Hastelloy C autocrave, and after evacuation under reduced pressure at 120° C., a fluorine gas diluted to 20% with nitrogen, was introduced at 50° C. The supply of the diluted fluorine gas was continued for 4 hours while purging under atmospheric pressure. Then, a fluorine gas diluted to 50% with nitrogen was sealed in the autocrave, and the temperature was raised to 200° C. and then maintained for two hours. After cooling to room temperature, the remaining fluorine gas was purged with nitrogen gas, and 800 g of $SbF_5$ and 400 g of hydrogen fluoride were charged.

The autocrave was heated to 100° C., and then the reaction was initiated by supplying tetrachloroethylene at an average supply rate of 80 g/hr (0.48 mol/hr) and hydrogen fluoride at an average supply rate of 60 g/hr (3 mol/hr) with stirring. The pressure for reaction was controlled to be from 11 to 12 $kg/cm^2G$, and the product was continuously distilled out together with hydrogen chloride produced as a byproduct and unreacted hydrogen fluoride from a condenser maintained at 90° C.

Organic components in the distilled gas after 24 hours are shown in Table 1 (unit: mol %). The reaction was terminated after 72 hours, and the test piece was recovered. The corrosion rate (unit: mm/year) of the test piece was measured, and the results are shown in Table 2.

EXAMPLE 4

A test piece for corrosion test of about 40 mm×10 mm×3 mm was attached to the inside of a 2l Hastelloy C autocrave, and after evacuation under reduced pressure at 120° C., 100 g of hydrogen fluoride was charged at room temperature. The temperature was raised to 120° C. and maintained for one hour. Then, hydrogen fluoride in the autocrave was purged, and nitrogen gas was introduced. After cooling the autocrave to room temperature, 800 g of $SbF_5$ and 400 g of hydrogen fluoride were charged.

The autocrave was heated to 100° C., and then tetrachloroethylene was fluorinated by hydrogen fluoride under the same conditions as Example 3 with stirring, whereby organic components in the distilled gas after 24 hours were substantially the same as in Example 3.

The reaction was terminated after 72 hours, and the test piece was recovered. The corrosion rate of the test piece was measured, and the results are shown in Table 3. In Table 3, the unit for the numerical values in the column for Material of the test piece is wt % (the same applies in Tables 4 to 7).

EXAMPLE 5

A test piece for corrosion test of about 40 mm×10 mm×3 mm was attached to the inside of a 2l Hastelloy C autocrave, and 800 g of $SbF_5$ and 400 g of hydrogen fluoride were charged.

The autocrave was heated to 100° C. and stirred for one hour. Then, tetrachloroethylene was fluorinated by hydrogen fluoride under the same conditions as in Example 3, whereby organic components in the distilled gas after 24 hours were substantially the same as in Example 3. The reaction was terminated after 72 hours, and the test piece was recovered. The corrosion rate of the test piece was measured, and the results are shown in Table 4.

EXAMPLE 6

A reaction was carried out in the same manner as in Example 5 except that the catalyst was changed from $SbF_5$ to $TaF_5$, and the average supply rates of tetrachloroethylene and hydrogen fluoride were changed to 60 g/hr and 45 g/hr, respectively. Organic components in the distilled gas after 24 hours are shown in Table 2, and the corrosion rate of the test piece recovered after 72 hours is shown in Table 5.

EXAMPLE 7

A reaction was carried out in the same manner as in Example 6 except that the catalyst was changed from $TaF_5$ to $NbF_5$, and the average supply rate of hydrogen fluoride was changed to 60 g/hr. Organic components in the distilled gas after 24 hours are shown in Table 1, and the corrosion rate of the test piece after recovered after 72 hours is shown in Table 6.

EXAMPLE 8

A reaction was carried out in the same manner as in Example 4 except that 80 g/hr of tetrachloroethylene was changed to 100 g/hr of methylene chloride, hydrogen fluoride was added at an average supply rate of 55 g/hr, the reaction temperature was changed to 80° C. and the pressure for reaction was changed to 10 $kg/cm^2G$. Organic components in the distilled gas after 24 hours are shown in Table 1, and the corrosion rate of the test piece recovered after 72 hours is shown in Table 7.

EXAMPLE 9

A test piece for corrosion test of about 40 mm×10 mm×3 mm was attached to the inside of a 2l Hastelloy C autocrave, and after deaeration under reduced pressure at 120° C., 100 g of hydrogen fluoride was charged at room temperature. The temperature was raised to 120° C. and maintained for one hour. Then, hydrogen fluoride in the autocrave was purged, and nitrogen gas was introduced. After cooling the autocrave to room temperature, 800 g of $SbF_5$ and 400 g of hydrogen fluoride were charged.

The autocrave was heated to 80° C., and then a reaction was initiated by supplying 1,1,1-trichloroethane at an average supply rate of 64 g/hr (0.48 mol/hr) and hydrogen fluoride at an average supply rate of 60 g/hr (3 mol/hr) with stirring. The pressure for reaction was controlled to be from 8 to 9 $kg/cm^2G$, and the product was continuously distilled out together with hydrogen chloride produced as a byproduct and unreacted hydrogen fluoride from a condenser maintained at 50° C.

Organic components in the distilled gas after 24 hours are shown in Table 1, and the corrosion rate of the test piece recovered after 72 hours is shown in Table 8.

EXAMPLE 10

A reaction was carried out in the same manner as in Example 9 except that 64 g/hr of 1,1,1-trichloroethane was changed to 48 g/hr of 1,1-dichloroethane, and hydrogen fluoride was added at an average supply rate of 40 g/hr. Organic components in the distilled gas after 24 hours are shown in Table 1, and the corrosion rate of the test piece recovered after 72 hours is shown in Table 9.

In Tables 2 to 9 and Tables 1 to 17, HC, SUS, I and Monel represent Hastelloy C (tradename for a nickel alloy), stainless steel, Inconel (tradename for a nickel alloy) and Monel (tradename for a nickel alloy), respectively.

TABLE 1

| Example No. | 1 | 2 | 3 | 6 | 7 | 8 | 9 | 10 |
|---|---|---|---|---|---|---|---|---|
| Catalyst | SbF$_5$ | SbF$_5$ | SbF$_5$ | TaF$_5$ | NbF$_5$ | SbF$_5$ | SbF$_5$ | SbF$_5$ |
| CF$_3$CHCl$_2$ | 93 |  | 93 | 90 | 65 |  |  |  |
| CClF$_2$CHCl$_2$ | 5 |  | 5 | 8 | 33 |  |  |  |
| CF$_3$CHClF | 0.5 |  | 0.5 | 0.1 |  |  |  |  |
| CH$_2$F$_2$ |  | 96 |  |  |  | 96 |  |  |
| CH$_2$ClF |  | 3.5 |  |  |  | 3.5 |  |  |
| Other | 1.5 | 0.5 | 1.5 | 1.9 | 2 | 0.5 |  |  |
| CH$_3$CCl$_2$F |  |  |  |  |  |  | 3 |  |
| CH$_3$CClF$_2$ |  |  |  |  |  |  | 12 |  |
| CH$_3$CF$_3$ |  |  |  |  |  |  | 79 |  |
| Other |  |  |  |  |  |  | 6 |  |
| CH$_3$CHClF |  |  |  |  |  |  |  | 8 |
| CH$_3$CHF$_2$ |  |  |  |  |  |  |  | 75 |
| Other |  |  |  |  |  |  |  | 17 |

TABLE 2

| Example No. | 3 | | | | |
|---|---|---|---|---|---|
| Material of the test piece | HC-276 | SUS304L | SUS316L | I-600 | Al |
| Corrosion rate (mm/y) | 1.90 | 32.8 | 41.6 | 18.9 | 0.01 |

TABLE 3

| Example No. | 4 | | | | | |
|---|---|---|---|---|---|---|
| Material of the test piece | HC-276 | Monel | Al | Al/Cu/Mn/Mg = 94.5/4/1/0.5 | Al/Mg/Cr = 97.3/2.5/0.2 | Al/Mg/Mn = 95/4/1 |
| Corrosion rate (mm/y) | 3.55 | 16.9 | 0.01 | 0.02 | 0.01 | 0.02 |

TABLE 4

| Example No. | 5 | | | | | |
|---|---|---|---|---|---|---|
| Material of the test piece | HC-276 | SUS304L | Fe/Cr/Al = 60/30/10 | Fe/Cr/Al/Co = 57/30/10/3 | Cu/Al = 88/12 | Al |
| Corrosion rate (mm/y) | 4.18 | 65.1 | 0.03 | 0.02 | 0.05 | 0.01 |

TABLE 5

| Example No. | 6 | | | | |
|---|---|---|---|---|---|
| Material of the test piece | SUS304L | SUS316L | Al | Al/Mg/Cr = 97.3/2.5/0.2 | Al/Mg/Mn = 95/4/1 |

TABLE 5-continued

| Example No. | 6 | | | | |
|---|---|---|---|---|---|
| Corrosion rate (mm/y) | 17.8 | 9.54 | 0.01 | 0.01 | 0.02 |

TABLE 6

| Example No. | 7 | | | | |
|---|---|---|---|---|---|
| Material of the test piece | SUS304L | SUS316L | Al | Al/Mg/Cr = 97.3/2.5/0.2 | Al/Mg/Mn = 95/4/1 |
| Corrosion rate (mm/y) | 35.8 | 35.2 | 0.01 | 0.01 | 0.02 |

TABLE 7

| Example No. | 8 | | | | | |
|---|---|---|---|---|---|---|
| Material of the test piece | HC-276 | SUS304L | 5U5316L | I-600 | Fe/Cr/Al = 60/30/10 | Al |
| Corrosion rate (mm/y) | 3.67 | 55.0 | 25.4 | 15.1 | 0.04 | 0.01 |

TABLE 8

| Example No. | 9 | | | | | |
|---|---|---|---|---|---|---|
| Material of the test piece | HC-276 | SUS304L | SUS316L | Al | Cu/Al = 88/12 | Fe/Cr/Al/Co = 58/30/10/2 |
| Corrosion rate (mm/y) | 0.50 | 1.2 | 1.0 | 0.00 | 0.01 | 0.01 |

TABLE 9

| Example No. | 10 | | | | | |
|---|---|---|---|---|---|---|
| Material of the test piece | HC-276 | SUS304L | SUS316L | Al | Cu/Al = 88/12 | Fe/Cr/Al/Co 58/30/10/2 |
| Corrosion rate (mm/y) | 1.50 | 8.2 | 5.0 | 0.01 | 0.05 | 0.08 |

EXAMPLE 11

A test piece for corrosion test of about 40 mm×10 mm×3 mm was attached to the inside of a 2l Hastelloy C autocrave, and after evacuation under reduced pressure at 120° C., a fluorine gas diluted to 20% with nitrogen was introduced at 50° C. The supply of the diluted fluorine gas was continued for 4 hours while purging under atmospheric pressure. Then, a fluorine gas diluted to 50% with nitrogen was sealed in the autocrave, and the temperature was raised to 200° C. and then maintained for two hours. After cooling to room temperature, the remaining fluorine gas was purged with nitrogen gas, and 800 g of SbF$_5$ and 400 g of hydrogen fluoride were charged.

The autoclave was heated to 80° C., and then the reaction was initiated by supplying 1,1,1,3,3-pentachloropropane at an average supply rate of 80 g/hr (0.37 mol/hr) and hydrogen fluoride at an average supply rate of 60 g/hr (3 mol/hr) with stirring. The pressure for reaction was controlled to be from 7.5 to 8.5 kg/cm²G, and the product was continuously distilled out together with hydrogen chloride produced as a byproduct and unreacted hydrogen fluoride from a condenser maintained at 70° C. Organic components in the distilled gas after 24 hours are shown in Table 10 (unit: mol %). The reaction was terminated after 72 hours, and the test piece was recovered. The corrosion rate (unit: mm/year) of the test piece was measured, and the results are shown in Table 11.

EXAMPLE 12

A test piece for corrosion test of about 40 mm×10 mm×3 mm was attached to the inside of a 2l Hastelloy C autoclave, and after evacuation under reduced pressure at 120° C., 100 g of hydrogen fluoride was charged at room temperature. The temperature was raised to 120° C. and maintained for one hour. Then, hydrogen fluoride in the autoclave was purged, and nitrogen gas was introduced. After cooling the autoclave to room temperature, 800 g of $SbF_5$ and 400 g of hydrogen fluoride were charged.

The autoclave was heated to 80° C., and then 1,1,1,3,3-pentachloropropane was fluorinated by hydrogen fluoride under the same conditions as in Example 11 with stirring, whereby organic components in the distilled gas after 24 hours were substantially the same as in Example 11. The reaction was terminated after 72 hours, and the test piece was recovered. The corrosion rate of the test piece was measured, and the results are shown in Table 12.

EXAMPLES 13 to 15

A test piece for corrosion test of about 40 mm×10 mm×3 mm was attached to the inside of a 2l Hastelloy C autoclave, and 800 g of $SbF_5$ and 400 g of hydrogen fluoride were charged.

The autoclave was heated to 80° C., and then stirred for one hour. Then, 1,1,1,3,3-pentachloropropane was fluorinated by hydrogen fluoride under the same conditions as in Example 11, whereby organic components in the distilled gas after 24 hours were substantially the same as in Example 11. The reaction was terminated after 72 hours, and the test piece was recovered. The corrosion rate of the test piece was measured, and the results are shown in Tables 12 to 14. In Tables 13 and 14, the unit for numerical values in the column for Material of the test piece is wt %.

EXAMPLE 16

A reaction was carried out in the same manner as in Example 13 except that the catalyst was changed from $SbF_5$ to $TaF_5$, and the supply rates of 1,1,1,3,3-pentachloropropane and hydrogen fluoride were changed to 60 g/hr and 45 g/hr, respectively. Organic components in the distilled gas after 24 hours are shown in Table 10, and the corrosion rate of the test piece recovered after 72 hours is shown in Table 15.

EXAMPLE 17

A reaction was carried out in the same manner as in Example 16 except that the catalyst was changed from $TaF_5$ to $NbF_5$. Organic components in the distilled gas after 24 hours are shown in Table 10, and the corrosion rates of four types of test pieces recovered after 72 hours are shown in Table 15.

TABLE 10

| Example No. | 11 | 16 | 17 |
| --- | --- | --- | --- |
| Catalyst | $SbF_5$ | $TaF_5$ | $NbF_5$ |
| $CF_3CH_2CHF_2$ | 95 | 90 | 80 |
| $CF_3CH_2CHClF$ | 0.5 | 3.0 | 8.8 |
| $CClF_2CH_2CHF_2$ | 0.1 | 0.5 | 1.2 |
| Olefins and Others | 4.4 | 6.5 | 10.0 |

TABLE 11

| Example No. | 11 | | | |
| --- | --- | --- | --- | --- |
| Material of the test piece | HC-276 | SUS304L | SUS316L | Al |
| Corrosion rate (mm/y) | 3.89 | 22.8 | 21.6 | 0.01 |

TABLE 12

| Example No. | 12 | 13 |
| --- | --- | --- |
| Material of the test piece | HC-276 | Al | Al |
| Corrosion rate (mm/y) | 4.25 | 0.02 | 0.01 |

TABLE 13

| Example No. | 14 | | | |
| --- | --- | --- | --- | --- |
| Material of the test piece | HC-276 | Al/Cu/Mn/Mg = 94.5/4/1/0.5 | Al/Mg/Cr = 97.3/2.5/0.2 | Al/Mg/Mn = 95/4/1 | Fe/Cr/Al = 60/30/10 |
| Corrosion rate (mm/y) | 4.76 | 0.02 | 0.02 | 0.03 | 0.03 |

TABLE 14

| Example No. | 15 | | | |
| --- | --- | --- | --- | --- |
| Material of the test piece | I-600 | Monel | Fe/Cr/Al/Co = 57/30/10/3 | Cu/Al = 88/12 |
| Corrosion rate (mm/y) | 6.89 | 8.43 | 0.05 | 0.08 |

TABLE 15

| Example No. | 16 | | 17 | |
| --- | --- | --- | --- | --- |
| Material of the test piece | SUS304L | SUS316L | Al | SUS304L | Al |

TABLE 15-continued

| Example No. | 16 | | 17 | | |
|---|---|---|---|---|---|
| Corrosion rate (mm/y) | 17.81 | 35.24 | 0.01 | 2.34 | 0.01 |

According to the present invention, it is possible to produce a hydrogen-containing fluorinated alkane in good yield over a long period of time on an industrial scale by using a reactor which is excellent in corrosion resistance and which is made of a material which is relatively inexpensive and industrially readily available.

What is claimed is:

1. A method for producing a hydrogen-containing fluorinated alkane, which comprises fluorinating at least one halogenated hydrocarbon selected from a chlorinated ethylene and a hydrogen-containing chlorinated alkane by hydrogen fluoride in the presence of a fluorination catalyst, in a reaction system where a corrosion-resistant metal material containing at least 10 wt. % of aluminum is present; and wherein at least a part of the surface of the corrosion-resistant metal material has a protective layer containing a metal fluoride.

2. The method according to claim 1, wherein the corrosion-resistant metal material is a corrosion-resistant metal material consisting substantially solely of aluminum.

3. The method according to claim 1, wherein the corrosion-resistant metal material is an alloy comprising aluminum and at least one metal selected from iron, copper, manganese, magnesium, cobalt and chromium.

4. The method according to claim 1, wherein the corrosion-resistant metal material constitutes the inner surface of a reactor.

5. The method according to claim 1, wherein the halogenated hydrocarbon is a chlorinated ethylene of the formula (1) $C_2H_aF_bCl_c$ wherein a, b and c are integers satisfying a+b+c=4, a$\geq$0, b$\geq$0 and c$\geq$1, and the hydrogen-containing fluorinated alkane is a hydrogen-containing fluorinated ethane of the formula (5) $C_2H_{a+1}F_{b+1+w}Cl_{c-w}$ wherein a, b, c and w are integers satisfying a+b+c=4, a$\geq$0, b$\geq$0, c$\geq$1 and 0$\leq$w$\leq$c.

6. The method according to claim 5, wherein the halogenated hydrocarbon is tetrachloroethylene, and the hydrogen-containing fluorinated ethane is 1,1-dichloro-2,2,2-trifluoroethane.

7. The method according to claim 1, wherein the halogenated hydrocarbon is a hydrogen-containing chlorinated methane of the formula (2) $CH_dF_eCl_f$ wherein d, e and f are integers satisfying d+e+f=4, d$\geq$1, e$\geq$0 and f$\geq$1, and the hydrogen-containing fluorinated alkane is a hydrogen-containing fluorinated methane of the formula (6) $CH_dF_{e+x}Cl_{f-x}$ wherein d, e, f and x are integers satisfying d+e+f=4, d$\geq$1, e$\geq$0, f$\geq$1 and 1$\leq$x$\leq$f.

8. The method according to claim 7, wherein the hydrogen-containing halogenated methane is methylene chloride, and the hydrogen-containing fluorinated methane is difluoromethane.

9. The method according to claim 1, wherein the halogenated hydrocarbon is a hydrogen-containing chlorinated ethane of the formula (3) $C_2H_gF_hCl_i$ wherein g, h and i are integers satisfying g+h+i=6, g$\geq$1, h$\geq$0 and i$\geq$1, and the hydrogen-containing fluorinated alkane is a hydrogen-containing fluorinated ethane of the formula (7) $C_2H_gF_{h+y}Cl_{i-y}$ wherein g, h, i and y are integers satisfying g+h+i=6, g$\geq$1, h$\geq$0, i$\geq$1 and 1$\leq$y$\leq$i.

10. The method according to claim 9, wherein the fluorine-containing halogenated ethane is 1,1,1-trichloroethane, and the hydrogen-containing fluorinated ethane is 1,1,1-trifluoroethane.

11. The method according to claim 9, wherein the hydrogen-containing halogenated ethane is 1,1-dichloroethane, and the hydrogen-containing fluorinated ethane is 1,1-difluoroethane.

12. The method according to claim 1, wherein the halogenated hydrocarbon is a hydrogen-containing chlorinated propane of the formula (4) $C_3H_mF_nCl_p$ wherein m, n and p are integers satisfying m+n+p=8, m$\geq$1, n$\geq$0 and p$\geq$1, and the hydrogen-containing fluorinated alkane is a hydrogen-containing fluorinated propane of the formula (8) $C_3H_mF_{n+z}Cl_{p-z}$ wherein m, n, p and z are integers satisfying m+n+p=8, m$\geq$1, n$\geq$0 p$\geq$1 and 1$\leq$z$\leq$p.

13. The method according to claim 12, wherein the hydrogen-containing halogenated propane is at least one member selected from a partial fluoride of 1,1,1,3,3-pentafluoropropane, and 1,1,1,3,3-pentachloropropane, and the hydrogen-containing fluorinated propane is 1,1,1,3,3-pentafluoropropane.

14. The method according to claim 1, wherein the fluorination catalyst is a fluorination catalyst containing a halide of at least one element selected from antimony, niobium and tantalum.

15. The method according to claim 1, wherein the fluorination reaction is carried out at a temperature of from 0° C. to 175° C.

16. The method according to claim 1, wherein the molar ratio of hydrogen fluoride supplied to the halogenated hydrocarbon is from 1 to 10 mols per the stoichiometrical amount.

17. The method according to claim 1, wherein the fluorination reaction is carried out under a pressure of from 0 to 20 kg/cm$^2$G.

18. The method according to claim 1, wherein the fluorination reaction is a liquid phase fluorination reaction.

* * * * *